(12) United States Patent
Brannan et al.

(10) Patent No.: US 11,490,881 B2
(45) Date of Patent: Nov. 8, 2022

(54) BATTERY ASSEMBLIES AND CONTROL METHODS THEREOF

(71) Applicant: Covidien LP, Mansfield, MA (US)

(72) Inventors: Edward L. Brannan, Erie, CO (US); Keith W. Malang, Longmont, CO (US); James R. Fagan, Erie, CO (US); Clifford D. Owens, Denver, CO (US)

(73) Assignee: Covidien LP, Mansfield, MA (US)

( * ) Notice: Subject to any disclaimer, the term of this patent is extended or adjusted under 35 U.S.C. 154(b) by 469 days.

(21) Appl. No.: 16/685,411

(22) Filed: Nov. 15, 2019

(65) Prior Publication Data

US 2021/0145420 A1     May 20, 2021

(51) Int. Cl.
*A61B 17/00*     (2006.01)
*H02M 3/158*     (2006.01)
*H02J 7/00*      (2006.01)

(52) U.S. Cl.
CPC ............ *A61B 17/00* (2013.01); *H02J 7/0029* (2013.01); *H02M 3/1582* (2013.01); *A61B 2017/00734* (2013.01); *H02J 2007/0067* (2013.01); *H02J 2207/20* (2020.01)

(58) Field of Classification Search
CPC ...... H02J 2207/40; H02J 7/00034; H02J 7/06; H02J 2007/0067; A61B 2018/00791; A61B 17/00; A61B 2017/320069; A61B 18/1233; A61B 17/07207; H02M 3/1582
See application file for complete search history.

(56) References Cited

U.S. PATENT DOCUMENTS

| | | | |
|---|---|---|---|
| 9,107,690 B2 | 8/2015 | Bales, Jr. et al. | |
| 9,314,261 B2 | 4/2016 | Bales, Jr. et al. | |
| 10,368,898 B2 | 8/2019 | Brown et al. | |
| 2009/0230923 A1* | 9/2009 | Hoffman | H02J 7/00714 320/136 |
| 2014/0113166 A1* | 4/2014 | Schneider | H01M 10/6571 219/494 |
| 2015/0157354 A1* | 6/2015 | Bales, Jr | A61B 50/20 606/169 |
| 2017/0164994 A1* | 6/2017 | Smith | H02J 50/10 |

* cited by examiner

*Primary Examiner* — Jared Fureman
*Assistant Examiner* — Duc M Pham
(74) *Attorney, Agent, or Firm* — Carter, DeLuca & Farrell LLP

(57) ABSTRACT

A battery assembly includes a battery pack configured to supply energy to a load having a required energy, a housing enclosing the battery pack therein, a converter configured to convert an internal energy of the battery pack, and a controller configured to adjust a parameter of the converter based on information received from the load via a communication interface such that the converter converts the internal energy to the energy required by the load, wherein the converted internal energy is supplied to the load as the supplied energy.

21 Claims, 9 Drawing Sheets

BATTERY ASSEMBLIES AND CONTROL METHODS THEREOF

FIELD

The disclosure is generally related to battery assemblies and control methods thereof, in particular, for use with various power sources and/or various surgical devices.

BACKGROUND

Various surgical devices have been developed for and are used in surgical operations. Due to various requirements of the surgical operations, surgical devices likewise require various forms of and/or levels of energy. For example, microwave ablation probes require a high frequency surgical energy and a high power for a relatively long period, while powered staplers require a relatively short burst of energy to fire a stapler. Likewise, power supplies, which supply energy to these surgical devices, need to meet these various requirements and forthcoming requirements.

Further, surgical devices have become increasingly mobile. Thus, portable battery packs have been used as the power supplies to power the surgical devices to perform surgical operations. Portable battery packs are typically recharged and reused. Thus, the portable battery packs need to meet the charging requirements of various external power sources.

SUMMARY

The aspects and features of this disclosure generally relate to battery assemblies and control methods for adapting the battery assemblies to be used as power sources in various different configurations, recharging the battery assemblies, and to various surgical devices powered by the battery assemblies. Further, safety features of the battery assemblies are also provided herein.

In one aspect, the present disclosure provides a battery assembly to provide energy to various devices. The battery assembly includes a battery pack configured to supply energy to a load having a required energy, a housing enclosing the battery pack therein, a converter configured to convert an internal energy of the battery pack, and a controller configured to adjust a parameter of the converter based on information received from the load via a communication interface such that the converter converts the internal energy to the energy required by the load, wherein the converted internal energy is supplied to the load as the supplied energy.

In another aspect, the converter is a buck-boost converter including a resistor.

In another aspect, the controller adjusts an impedance value of the resistor to configure the converter into a buck converter or a boost converter based on comparison between the internal energy and the required energy.

In another aspect, the load is a surgical device.

In another aspect, the battery assembly further includes a memory configured to store a programmable configuration file, which includes a plurality of settings of the converter.

In another aspect, the plurality of settings included in the programmable configuration file are modified according to characteristics of the battery assembly. The characteristics include a size of a battery cell in the battery pack, a chemistry of a battery cell in the battery pack, and tolerance ranges of the battery pack.

In another aspect, the battery assembly further includes a sensor configured to sense the supplied energy to the load to generate sensed results.

In still another aspect, the controller measures parameters of the supplied energy, compares the measured parameters with reference values included in the information, and controls the converter to adjust a level of the supplied energy.

In still another aspect, the converter includes an h-bridge with an inductor as a crossbar.

In still another aspect, the inductor is to be scaled to accommodate energy required by the load when the required energy is outside of an operational range of the battery pack.

In still another aspect, the controller adjusts an impedance value of a resistor in the h-bridge based on the measured parameters.

In still another aspect, the controller generates a pulse-width-modulation (PWM) signal to adjust a duty cycle of the h-bridge.

In still another aspect, the controller is further configured to measure at least one of a voltage or a current the supplied energy based on the sensed results.

In still another aspect, the controller is further configured to compare the measurement with the required energy and generate a feedback signal to control the converter based on the feedback signal.

In still another aspect, the battery assembly further includes a safety device configured to stop delivery of the supplied energy to the load in an emergency condition.

In still another aspect, the emergency condition occurs when a current of the supplied energy falls outside of an operable current range or when a temperature of the battery pack falls outside of an operable temperature range.

In still another aspect, the safety device is a separator between an anode and a cathode of the battery pack.

In yet still another aspect, the safety device is a pressure relief vent configured to open a connection between internal and external positive terminals of the battery pack when a heat generated by the battery pack causes a pressure within the battery pack to go over a threshold pressure.

In one aspect, the present disclosure provides a method for controlling a battery assembly. The method includes connecting the battery assembly to a load, the load having a required energy, receiving information from the load via a communication interface between the battery assembly and the load, comparing an internal energy of the battery assembly with the required energy of the load, which is obtained from the information, configuring a converter of the battery assembly as a buck converter or a boost converter based on the comparison, and controlling the converter to supply energy, as a supplied energy, to the load via an output port.

In another aspect, the method further includes sensing parameters of the supplied energy to generate a feedback signal, and controlling the converter based on the feedback signal so that a voltage of the supplied energy follows a voltage of the required energy.

In still another aspect, the converter includes an h-bridge with an inductor as a crossbar.

In still another aspect, the method further includes configuring the converter includes adjusting an impedance value of a resistor in the h-bridge.

In still another aspect, the method further includes generating a pulse-width-modulation (PWM) signal based on the feedback signal. A duty cycle of the h-bridge is adjusted based on the PWM signal.

In still another aspect, the method further includes stopping supply of the supplied energy when an emergency occurs.

In still another aspect, the emergency occurs when a current of the supplied energy goes over a threshold current or when a temperature of the battery assembly is over a threshold temperature.

In one aspect, the present disclosure provides a battery assembly to be recharged by various power sources. The battery assembly includes a battery pack configured to be recharged by a power source configured to supply an input voltage to the battery pack, a housing encompassing the battery pack, a converter configured to convert the input voltage supplied by the power source to an internal voltage to recharge the battery pack, and a controller configured to adjust a parameter of the converter based on the input voltage.

In another aspect, the battery assembly includes a rectifier configured to convert the input voltage to a direct voltage when the input voltage is an alternating voltage.

In another aspect, the converter includes an h-bridge with an inductor as a crossbar.

In still another aspect, the controller is further configured to adjust the inductor or semiconductor switch network in the h-bridge when the input voltage is outside of an operational range of the battery pack.

In still another aspect, the converter is a buck-boost converter.

In still another aspect, the controller controls the converter to be a buck converter or a boost converter based on comparison between the input voltage and the internal voltage.

In still another aspect, the battery assembly further includes a safety device configured to stop recharging the battery pack in an emergency condition.

In still another aspect, the emergency condition occurs when the input voltage falls outside of an operable voltage range or when a temperature of the battery pack falls outside of an operable temperature range.

In still another aspect, the safety device is a separator between an anode and a cathode of the battery pack.

In yet still another aspect, the safety device is a pressure relief vent configured to open a connection between internal and external positive terminals of the battery pack when a heat generated by the battery pack causes a pressure within the battery pack to go over a threshold pressure.

In one aspect, the present disclosure provides a portable surgical system, which includes a surgical device requiring a required energy to perform a surgical operation, and a battery assembly configured to couple to the surgical device and provide the required energy to the surgical device. The battery assembly includes a battery pack configured to supply energy to the surgical device, a housing enclosing the battery pack therein, a converter configured to convert an internal energy of the battery pack, and a controller configured to adjust a parameter of the converter based on information received from the surgical device via a communication interface such that the converter converts the internal energy to the energy required by the surgical device, wherein the converted internal energy is supplied to the surgical device as the supplied energy.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various aspects and features of the present disclosure are described below with reference to the drawings wherein like numerals designate identical or corresponding elements in each of the several views.

DETAILED DESCRIPTION

It is to be understood that the disclosed embodiments are merely exemplary and can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting; but rather, to provide an understandable description of the embodiments.

Various aspects of battery assemblies, as disclosed herein, resolve issues related to various power source configurations for outputting different powers, and to various devices requiring different power levels for connection to a battery assembly. Thus, the battery assemblies of this disclosure are capable of being recharged by various power sources and adjusting power output to meet the requirements of various devices.

Figure 1:
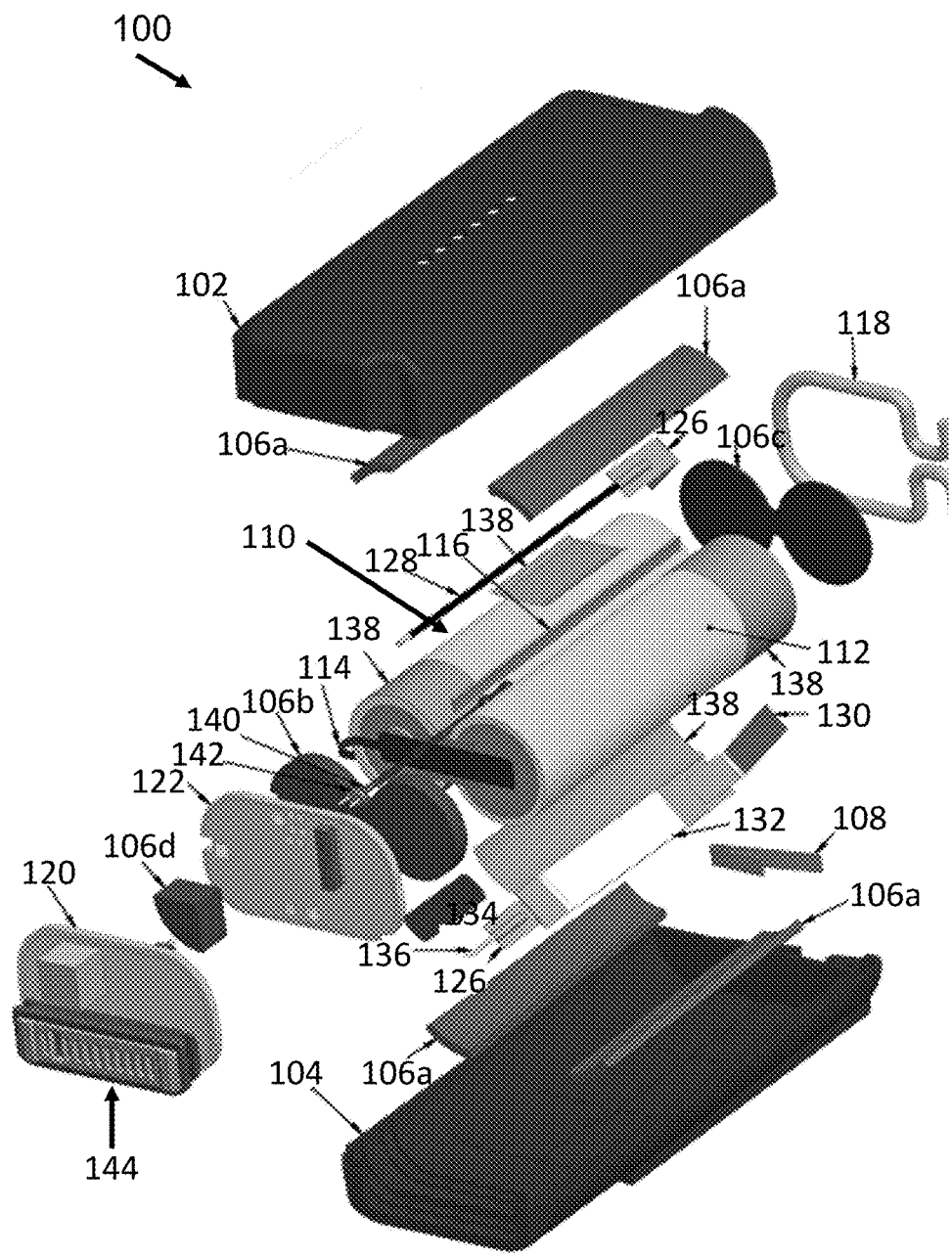
FIG. 1 is an exploded view of a battery assembly in accordance with the present disclosure.

FIG. 1 illustrates an exploded view of a battery assembly 100, which can accommodate recharge by various power sources and can supply energy to various connectable devices in accordance with embodiments of the present disclosure. The battery assembly 100 includes a first housing portion 102, a second housing portion 104, and a battery pack 110. When the first housing portion 102 is mated with the second housing portion 104, an internal cavity is defined by the mated housing portions 102 and 104 to receive and enclose the battery pack 110.

The battery assembly 100 further includes shock absorbing elements 106a-106d so that the battery pack 110 is securely housed within the mated housing portions 102 and 104 and movements thereof can be prevented within the mated housings. Such shock absorbing elements 106a-106d may take various forms positioned around the interior of the mated housing portions 102 and 104 to provide cushions between the battery pack 110 and the mated housing portions 102 and 104. In aspects, the shock absorbing elements 106a-106d may be shaped as a long strip. For example, four shock absorbing elements 106a have a strip shape and are attached to the housing portions 102 and 104. Specifically, the shock absorbing elements 106a are positioned along the length directions of the housing portions 102 and 104, two shock absorbing elements 106a on the interior surface of each housing portion 102 and 104.

The battery pack 110 may be a collection of one or more battery cells 112. As shown in FIG. 1, the battery pack 110 includes two battery cells 112. However, the number of battery cells 112 may be one or more than two depending on requirements of the battery assembly 100. That is, generally, the higher the demand of energy, the more battery cells 112 needed. The shape of the battery cell 112 may be a cylinder, as shown, or any other suitable shape. The housing portions 102 and 104 may be shaped in a way so that the housing portions 102 and 104 can securely house the battery cell 112.

In configurations when the battery cell 112 has a cylindrical shape, the four shock absorbing elements 106a are positioned to contact the cylindrical-shaped battery cells 112 to inhibit direct contact between the battery cells 112 and the housing portions 102 and 104. In an aspect, the size of the shock absorbing elements 106a may be determined by this contact area of the battery cells 112. Further, the housing portions 102 and 104 may have a pattern on each inside surface thereof such that the shock absorbing elements 106a are easily attached at these contact areas.

The battery cells 112 may be glued together with an adhesive 116, which prevents the battery cells 112 from moving relative to each other when housed in the housing portions 102 and 104. The adhesive 116 may be Cyanoacrylate/UV glue or any other types of glue or other suitable adhesive for adhering the battery cells 112 together without corroding the outer housing of each battery cell 112.

As described above, the battery pack 110 is a collection of one or more battery cells 112. When the battery cells 112 are connected to each other, the connection may be in parallel or series. Where a series connection is used, the cathode (positive terminal) of one battery cell 112 is connected to the anode (negative terminal) of the other battery cell 112 via an electrical bridge 114, which may be a metal strip. In an aspect, the electrical bridge 114 may be a metal strip formed of copper, nickel, silver, or any conducting metals having a low resistance value. In an aspect, the connection of the battery cells 112 may be in any combination of parallel and series corresponding to the requirements of the connected device.

The battery assembly 100 further includes a fuel gauge 122 and a converter 120. The fuel gauge 122 may estimate parameters of the battery cells 112. For example, the parameters of the battery cells 112 may be battery state-of-charge, battery aging, error logs, etc. The fuel gauge 122 may estimate the parameters of each battery cell 112 and/or of the battery pack 110 as a whole.

The fuel gauge 122 may perform functions of a battery management module, which may include a processor and a memory or may be a computing device. The fuel gauge 122 may track impedance of the battery pack 110 so as to track aging of the battery pack 110. Further, the fuel gauge 122 may measure voltage, current, and temperature output by the battery pack 110 and also measure voltage, current, and temperature at the output port, which is to be connected to a surgical device. Based on the measurements, the fuel gauge 122 may provide protections when abnormal situations occur.

The fuel gauge 122 may further include a memory to record battery logging and a use count to keep track of general health of the battery assembly 100. Furthermore, the fuel gauge 122 may provide a real time clock so that any record stored in the memory may have a timestamp.

In an aspect, the fuel gauge 122 may be implemented on a printed circuit board (PCB). Likewise, the converter 120 may be implemented on another PCB.

The fuel gauge 122 is coupled to the battery pack 110 via the electrical bridge 114, a transmission wire 136, and a transmission wire 128. Thus, the fuel gauge 122 may be powered by the battery pack 110 and is able to perform necessary functions as the battery management module. As such, the electrical bridge 114 may have a metal protrusion therefrom, which is to connect to the fuel gauge 122.

The converter 120 converts an input power to an output power. The converter 120 may work as a buck converter when the input voltage is greater than the output voltage and as a boost converter when the input voltage is less than the output voltage. In other words, the converter 120 may be a buck-boost converter. The converter 120 may be a variable buck-boost converter.

In an aspect, the converter 120 may be used to charge the battery pack 110 or the battery cells 112. In this case, the battery assembly 100 is connected to an external power source. Since external power sources may output different powers, the voltages of external power sources may be different from each other. When the voltage output by the external power source is greater than the battery voltage for the battery cell 112, the converter 120 may be configured to work as a buck converter so as to reduce the output voltage of the external power source to the battery voltage. When the output voltage of the external power source is less than the battery voltage, the converter may be configured to work as a boost converter so that the output voltage of the external power source is amplified to be the battery voltage.

In a similar way, when the required voltage is less than the battery voltage, the converter 120 may work as a buck converter, and when the required voltage is greater than the battery voltage, the converter 120 may work as a boost converter to amplify the battery voltage to the required voltage.

To enable use with an external power source that outputs an alternative voltage (AC voltage), the battery assembly 100 may include a rectifier (not shown) to convert the AC voltage to a direct voltage (DC voltage), which is input to the converter 120. In this way, the AC voltage can be converted to a DC voltage suitable for recharging the battery cells 112.

In another aspect, the converter 120 may provide energy to a surgical device or a generator for the surgical device. Supply of energy by the converter 120 is not limited to surgical devices but can be expanded to any non-surgical devices, of which power can be supplied by the battery assembly 100. The converter 120 may convert the battery voltage from the battery cells 112 to a voltage required by the connected device. For this purpose, the battery assembly 100 further includes an array of contacts 144. The connected device may receive power through some of the array of contacts 144 and may communicate with the battery assembly 100 through the array of contacts 144.

When the device is connected to the battery assembly 100, the device may provide information to the battery assembly 100 through the array of contacts 144. The information may include voltage, current, power, duration of use, model number, manufacturer, etc. related to the connected device. Upon reception of the information, the battery assembly 100 may configure the converter 120 in a manner to supply the required voltage, current, and energy to the connected device.

For example, when the required voltage is greater than the battery voltage, the converter may be configured as a boost converter to amplify the battery voltage to the required voltage. In the same way, when the required voltage is less than the battery voltage, the converter may be configured as a buck converter to decrease the battery voltage to the required voltage.

When the required voltage is received and supply of the energy is requested from the connected device, the converter 120 may be controlled by itself to generate the required voltage in the initial stage. In this way, the required voltage may be generated and supplied to the connected device in a fast pace.

After the initial stage and while suppling the energy, the fuel gauge 122 may estimate voltage, current, power, or any combination thereof, which is provided to the connected device, and constantly compare the estimates with reference values obtained. Specifically, sensors (not shown) may generate digitized sensed signals and the fuel gauge 122 may estimate values for the parameters. Based on the estimated values of the parameters, the fuel gauge 122 then generates a pulse-width modulation (PWM) signal to control the converter 120 so that the converter 120 can adjust the output level to follow the reference values.

Figure 5:
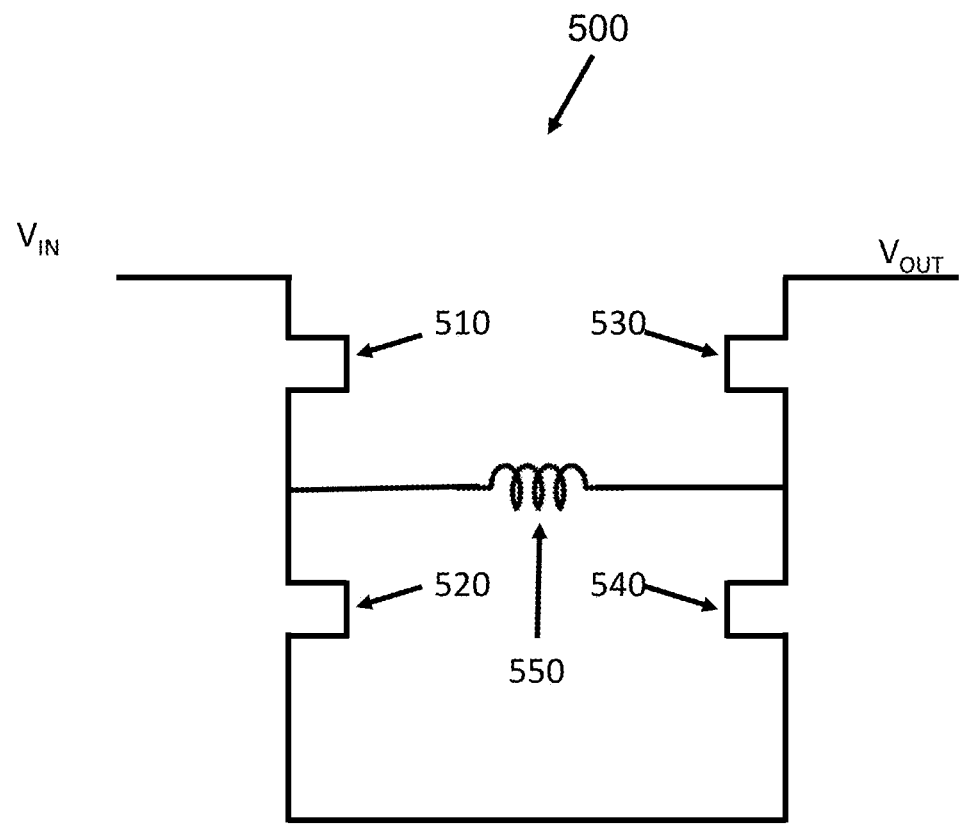
FIG. 5 is a circuit diagram of a buck-boost converter of the battery assembly of FIG. 1 in accordance with the present disclosure.

In this case, the converter 120 may include an h-bridge with an inductor as a crossbar, as shown in FIG. 5 and as detailed below. In particular, the fuel gauge 122 may generate a digital PWM signal, which is converted by a digital to analog converter (DAC). The analog PWM signal then controls the h-bridge to increase or decrease the output level. In an aspect, the PWM signal may control a duty cycle of the h-bridge.

The converter 120 may include a temperature sensor, which may be fixedly attached to the converter 120. While the converter 120 outputs energy, the temperature of the output stage of the converter 120 generally increases. In this regard, the temperature sensor may monitor temperature of the output stage of the converter 120, and prevent the delivery of energy output from the converter 120 when the monitored temperature of the output stage exceeds a predetermined range of temperatures. Once the temperature of the output stage falls in an acceptable range, then the delivery of the energy is resumed.

Continuing with reference to FIG. 1, another shock absorbing element 106b may be positioned between the converter 120 and the electrical bridge 114 to provide cushion therebetween. Further, the shock absorbing element 106b may also provide insulating effect therebetween. Also, the shock absorbing element 106d may be positioned between the converter 120 and the fuel gauge 122.

The shock absorbing element 106c may be positioned between a bottom end of the mated housing portions 102 and 104 and a bottom end of the battery pack 110. This shock absorbing element 106c also provides cushion therebetween. Thus, the shock absorbing elements 106b-106d prevent the battery pack 110 from moving in the length direction of the battery assembly 100, while the shock absorbing element 106a prevent the battery pack 110 from moving in the width direction of the battery assembly 100. Further, by providing a distance between the battery pack 110 and the other electrical circuit elements, the shock absorbing elements 106a-106d may provide insulation effects.

In an aspect, the shock absorbing elements 106a-106d may be made of any material which provides cushioning effects to prevent the battery pack 110 from moving inside the mated housings 102 and 104. Further, the shock absorbing elements 106a-116d may be made of insulative and non-conductive materials.

Regarding electrical connections, the battery assembly 100 includes a transmission strip 126 and a transmission wire 128, of which both form a connection between the negative terminal of one of the battery cells 112. In particular, the transmission strip 126 provides an electrical connection between the negative terminal and the transmission wire 128, and the transmission wire 128 provides an electric connection between the transmission strip 126 and the fuel gauge 122.

The battery assembly 100 further includes a transmission strip 130, a transmission wire 136, and a fuse 132. The transmission strip 130 provides an electrical connection between the positive terminal of a battery cell 112 and the fuse 132, and the transmission wire 136 provides an electrical connection between the fuse 132 and the fuel gauge 122. The transmission wire 136 may be a 19 gauge solid copper wire and the transmission wire 128 may be insulated 18 gauge solid wire.

The fuse 132 provides safety in overcurrent situations. When the current flowing through the fuse 132 goes over a predetermined current, the fuse 132 melts, thereby interrupting the current. In an aspect, the fuse 132 may be a positive temperature coefficient (PTC) fuse, which maintains its resistance low under normal operating condition. However, the PTC fuse heats up and its resistance increases sharply when overcurrent occurs. In another aspect, the fuse 132 may be a resettable fuse.

In a case where the battery pack 110 includes two or more battery cells 112, the battery cell 112 having the positive terminal, which is connected to the transmission strip 126 may be different from the battery cell 112 having the negative terminal, which is connected to the transmission strip 130. In a case when the battery pack 110 includes one battery cell 112, the transmission strips 126 and 130 are connected to the positive and negative terminals of the same battery cell 112, respectively.

The transmission wire 136 may be made of copper, nickel, silver, gold, or any conductive material. In an aspect, the transmission wire 136 may be a solid copper wire. An insulator 134 may be positioned in a way to insulate the transmission wire 136.

Further, each battery cell 112 may be taped around the cathode thereof by an insulative tape 138. As shown in FIG. 1, the insulative tape 138 encircles a cylindrical portion near the cathode of each battery cell 112. This taping ensures insulation for the battery cells 112.

Figure 2:
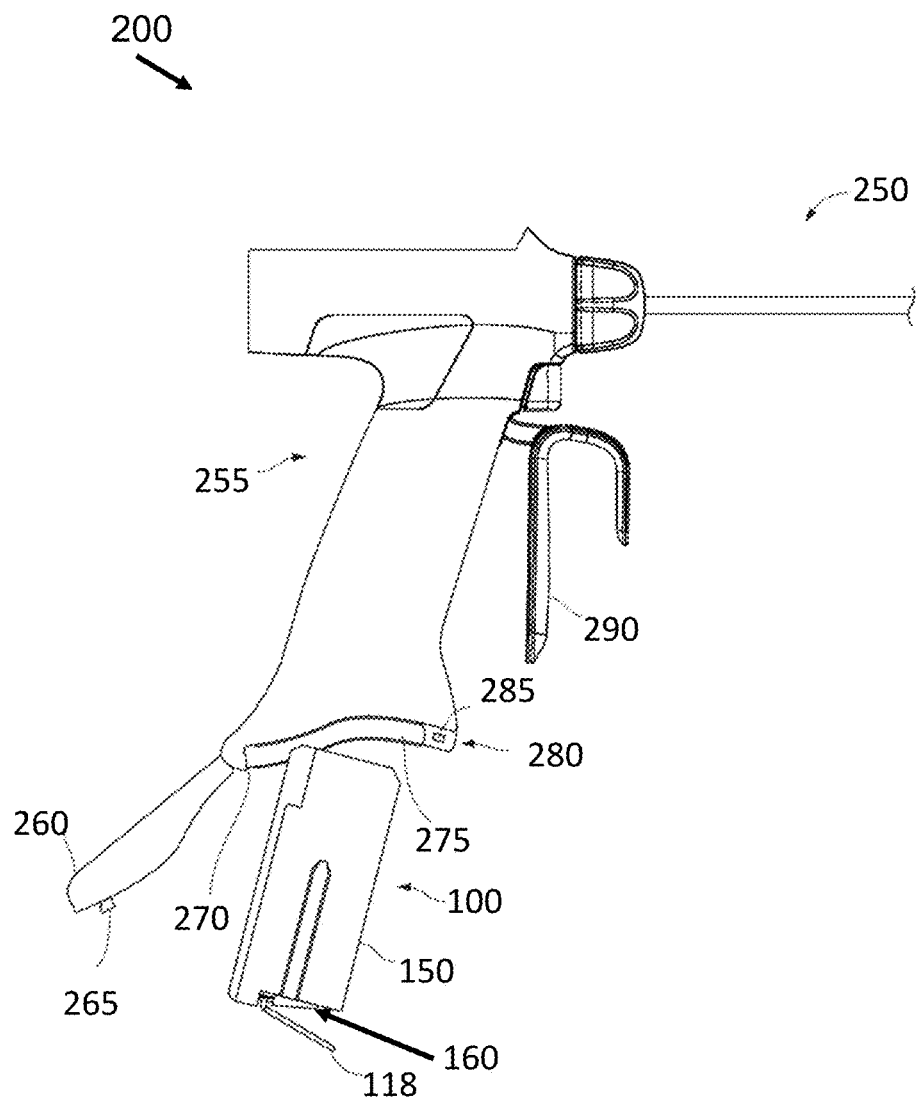
FIG. 2 is a side view of a surgical device and the battery assembly of FIG. 1 exploded therefrom in accordance with the present disclosure.

FIG. 2 illustrates a system 200 including an ultrasonic surgical device 250 and the battery assembly 100 in accordance with embodiments of the present disclosure. The ultrasonic surgical device 250 is an example of a surgical device, which can be connected with and supplied power by the battery assembly 100. For example, the system 200 may include a stapler, microwave ablator, dissector, endoscope, biopsy tool, end effector, etc., to which the battery assembly 100 can supply energy. This list of surgical devices is not exhaustive but can include any surgical/non-surgical devices, of which power can be supplied by the battery assembly 100. Further, FIG. 2 illustrates how the battery assembly 100 is connected with and removed from the ultrasonic surgical device 250.

The array of contacts 144 is disposed at the top end of the battery assembly 100. The hinge block 160 is disposed at a bottom end of the outer housing 150 and may be integrally formed therewith. The outer housing 150 houses the battery pack 110 and other battery circuitry (e.g., 120, 122, and other safety related elements) of the battery assembly 100. The array of contacts 144 provides an interface between the battery assembly 100 and the ultrasonic surgical device 250. Further, through the array of contacts 144, the battery assembly 100 may supply the energy to the ultrasonic surgical device 250.

The ultrasonic surgical device 250 includes a handle 255, of which inside defines a battery compartment 275 for receiving the battery assembly 100. The handle 255 has two parts, a stationary handle and a movable handle 290. When a user pulls the movable handle 290 toward the stationary part of the handle 255, the ultrasonic surgical device 250 is activated, e.g., to clamp tissue between a clamp jaw and an ultrasonic blade (not shown), and able to perform a surgical operation with supply of energy thereto.

The ultrasonic surgical device 250 includes a locking mechanism, which is composed of a door 260, a locking foot 265, a hinge 270, a locking aperture 280, and a release button 285. The door 260 is pivotable about the hinge 270 at the near side of the door 260. The locking foot 265 is positioned at the far side of the door 260 and includes a protrusion at the end of the locking foot 265 toward outside. When the protrusion of the locking foot 265 engages with the locking aperture 280, the door 260 is securely closed. When the release button 285 is pressed, the locking foot 265 is released from the locking aperture 280, thereby opening the door 260. Now, engagement and release of the battery assembly 100 with respect to the ultrasonic surgical device 250 is described in detail below.

Now referring back to FIG. 1, the battery assembly 100 includes an outer housing 150, which is a combination of the first half housing 102 and the second half housing 104, and a handle member 118. The hinge block 160 defines a slot and a pair of lumens, each of which is disposed near one end of the slot to enable pivotable coupling of the handle member 118 with the hinge block 160 of the outer housing 150, as detailed below. The spring member 108 of FIG. 1 takes any form of a torsion spring, leaf spring, plunger mechanism, etc.

The handle member 118 of the battery assembly 100 may be formed from a single piece of wire stock wherein the ends thereof define hinge legs and the body thereof is bent to define a finger ring portion and an extension portion, although other configurations are also contemplated. The finger ring portion defines an opening in the handle member 118 configured to receive a user's finger to facilitate grasping and manipulation of the battery assembly 100. The opening may be sufficiently dimensioned to enable positioning of the user's finger about the hinge block 160. Further, the opening may be equal to the dimensions of the bottom end of the outer housing 150 of the battery assembly 100 so as not to extend outwardly therefrom. Thus, the opening does not interfere with the insertion of the battery assembly 100 into the battery compartment 275 of a fixed handle 255 of the ultrasonic surgical device 250.

The handle member 118 is pivotable about a hinge of the hinge block 160 and rotatable from an initial position, where the user's hand can grasp the opening, to a storing position, where the handle member 118 can rest on the bottom end of the outer housing 150.

The handle member 118 and the spring member 108 are relatively positioned such that, as the handle member 118 is pivoted about the hinge and relative to the bottom end of the outer housing 150 from the initial position towards the storing position, the handle member 118 contacts the spring member 108 prior to reaching the stored position. Thus, in order to fully pivot the handle member 118 to the stored position, the handle member 118 must be sufficiently pressed against the spring of the spring member 108 and flex the spring member 108 towards the bottom end of the outer housing 150. Likewise, upon removal of the battery assembly 100 by removing a holding force retaining the handle member 118 in the stored position, the spring member 108 is resiliently returned outwardly under its spring, thereby releasing the handle member 118 to pivot from the stored position back towards the initial position. The spring constant and configuration of the spring member 108 as well as the relative position of the spring member 108 and the handle member 118 may be selected to achieve a desired point-at-which the handle member 118 contacts the spring member 108 and point-to-which the handle member 118 is returned under the bias of the spring member 108.

It is contemplated that the positioning of the handle member 118 in the returned position, where the handle member 118 is returned from the spring member 108, is sufficiently spaced apart from the bottom end of the outer housing 150, thereby readily enabling grasping and manipulation of the opening of the handle member 118 to facilitate insertion and removal of the battery assembly 100 from the battery compartment 275 of the handle 225 of the ultrasonic surgical device.

When the user pushes the battery assembly 100 back into the battery compartment 275 and the handle member 118 is pushed to the storing position, the door 260 of the ultrasonic surgical device 250 is closed or a far side of the door 260 rotates to the closing position. A locking foot 265, which is positioned in the far side of the door 260, is inserted into the locking aperture 280, which is positioned in the far side of the bottom of the handle 255. Upon full engagement of the locking foot 265 into the locking aperture 280, the door 260 is securely closed and the battery assembly 100 is then likewise securely stored inside of the battery compartment 275.

Upon full engagement of the battery assembly 100, the ultrasonic surgical device 250 may be powered from the battery assembly 100. Ultrasonic surgical device 250, including the use thereof, is described in greater detail, for example, in U.S. Pat. No. 10,368,898 (which issued based upon U.S. patent application Ser. No. 15/496,241), the entire contents of which are hereby incorporated herein by reference.

After performing the surgical operation, the user opens the door 260 by activating a release button 285, which may be a button or a pressure sensor. The locking foot 265 is then released from the locking aperture 280. The handle member 118 is presented, under bias, from the storing position to the initial position, to enable the user to grasp and pull, using the opening of the handle member 118, to remove the battery assembly 100 from the battery compartment 275.

Engagement and release mechanisms for the battery assembly 100 may be differently implemented in other devices, as can be readily implemented by a person having ordinary skill in the art.

Figure 3:
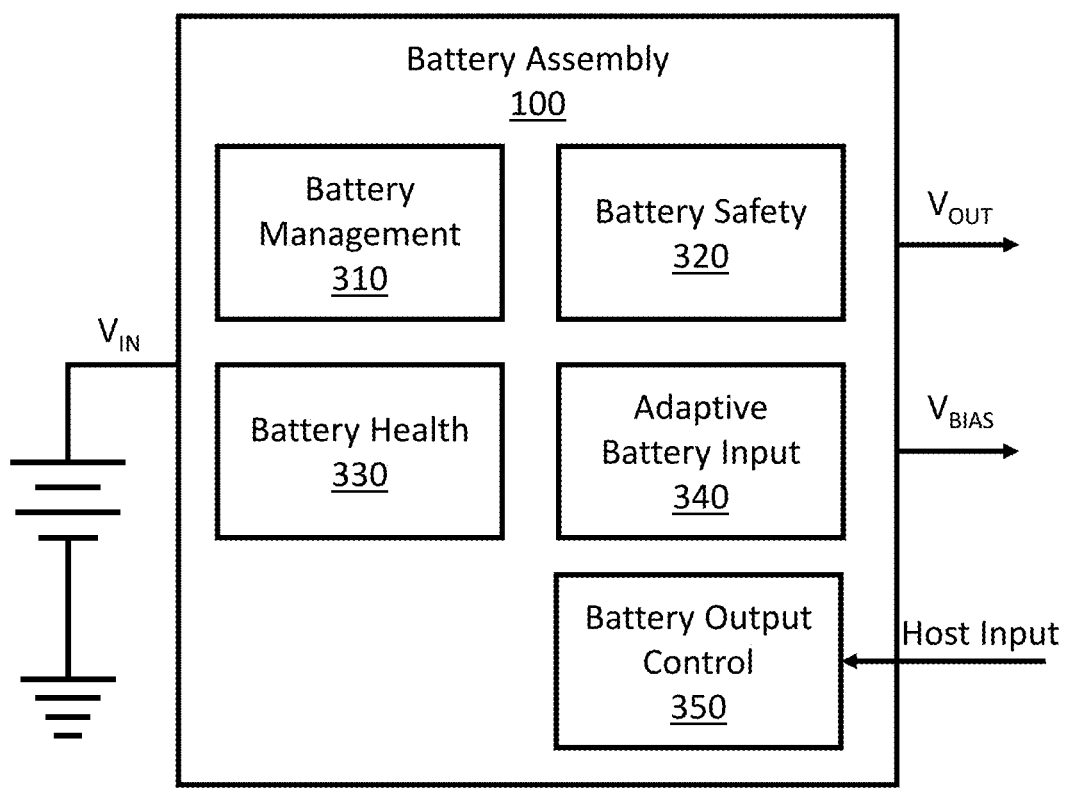
FIG. 3 is a functional block diagram of the battery assembly of FIG. 1 in accordance with the present disclosure.

FIG. 3 illustrates a functional block diagram of the battery assembly 100 of FIG. 1 in accordance with embodiments of present disclosure. As described above, the battery assembly 100 may include a processor and a memory including instructions. The processor may perform functions of the battery assembly 100 when executing the stored instructions. Further details of the processor and the memory will be disclosed below with reference to FIG. 7.

The battery assembly 100 may perform functions of a battery management module 310, a battery safety module 320, a battery health module 330, an adaptive battery input module 340, and a battery output control module 350. For example, when an external power source provides power, which has an input voltage $V_{IN}$, to the battery assembly 100, the battery management module 310 may check whether or not the input voltage $V_{IN}$ is within an operable range of the battery assembly 100.

In a case where the input voltage $V_{IN}$ is outside of the operable range, the battery management module 310 may change a resistance value of a resistor in the converter 120 of FIG. 1. In an aspect, the converter 120 may the battery management module 310 to adapt to the input voltage $V_{IN}$. Further, in a case where the temperature of the battery assembly 100 or the temperature of the battery cells 112 (FIG. 1) falls outside of the operable range thereof, the battery management module 310 may interrupt or terminate functions of the battery assembly 100 so as to prevent irreparable damages thereto.

Figure 4A:
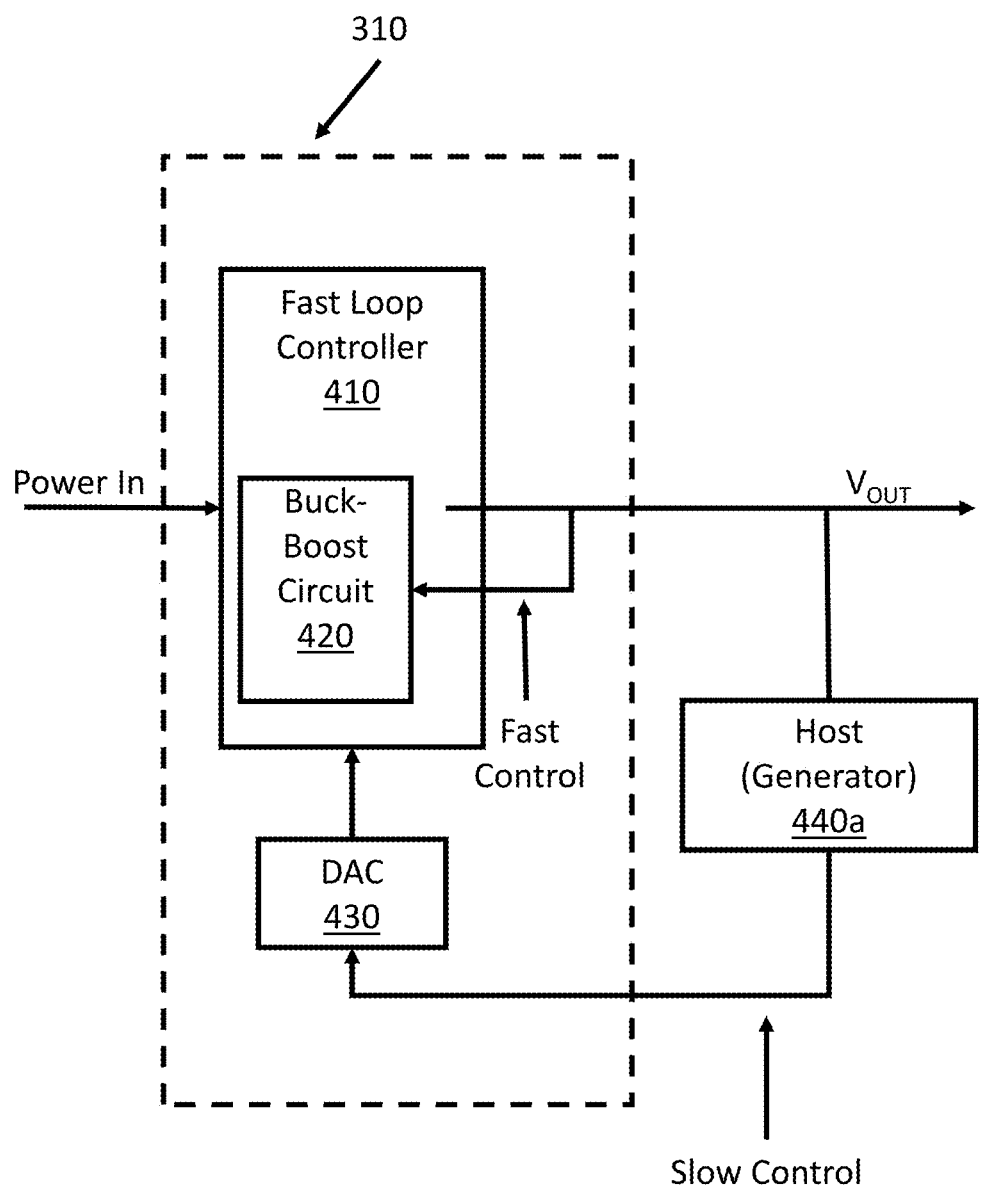
FIGS. 4A and 4B are block diagrams illustrating the battery management module and battery output control module of FIG. 3 in accordance with the present disclosure.

With reference to FIG. 4A, the battery management module 310 may include a fast loop controller 410, which includes a buck-boost circuit 420. In a fast mode, the battery management module 310 may internally control the converter buck-boost circuit 420 to adapt to the input voltage VIN to charge the battery pack 110 in a relatively short time.

For a slow mode, the battery management module 310 may include a digital-to-analog (DAC) converter 430. The battery management module 310 controls the buck-boost circuit 420 to charge the battery pack 110. The host 440a (e.g., a charge controller) may monitor the charge of the battery pack 110 and provide a feedback to the DAC 430 based on the level of the charge of the battery pack 110. The DAC 430 converts the feedback signal, which is an analog signal, to a digital signal so as to control the operation of the buck-boost circuit 420.

With additional reference to FIG. 1, the battery safety module 320 may be implemented in the hardware and/or in software in several elements of the battery assembly 100. Regarding the hardware safety features, the battery pack 110 may include a separator and a top cap assembly (not explicitly shown). Generally, there is a separator between an anode and a cathode within a battery cell 112. The separator utilizes a heat resistant layer (HRL) that adapts a high heat resistance resin to inhibit the short point in the separator when an internal short circuit occurs, e.g., by a particle piercing the separator and shorting the anode to the cathode. As the separator is heated, the resin within the HRL will flow and attempt to close the void in the separator caused by the particle. A short circuit will create heat and the more area shorted between the anode and cathode will cause this heat to increase. The separator limits this growth in the shorting area and thus improves the thermal stability of the battery cells 112.

The second hardware protection is the top cap assembly (not explicitly shown), which houses a current interrupt device (CID). The CID is a pressure relief vent that once opened, opens the connection between the internal and external positive terminal of the battery and interrupts the flow of current from the battery cells 112 to the positive terminal. The CID opens if the heat being generated by the battery cells 112 causes the pressure within the battery cells 112 to exceed a certain point.

Furthermore, the battery assembly 100 has hardware components, as a part of the battery safety module 320, external to the battery pack 110. The fuel gauge 122 may include and control switches that enable charging/discharging of the battery cells 112. The switches may be field-effect transistors (FETs). By controlling the charge/discharge FETs, the fuel gauge 122 may control the flow of current within the battery assembly 100.

In an aspect, the fuel gauge 122 may include a reverse polarity FET, which provides forced discharge protection and works with the discharge FET to prevent discharge if reverse polarity is applied to the battery pack 110. Once tripped, the fuel gauge 122 is permanently prohibited from enabling the discharge FET. The purpose for the reverse polarity FET is to protect the battery cells 112.

The fuse 132 of the battery assembly 100 may be resettable and not controlled by the fuel gauge 122. When tripped, this opens the current path from the battery cells 112 to the array of contacts 144, thereby preventing current flow from the battery.

In another aspect, the battery assembly 100 may include a secondary over-voltage protection device (e.g., external over-voltage integrated circuit (IC)), which is separate, redundant, and independent from the fuel gauge 122. The secondary over-voltage protection device monitors each battery cell 112 for over-voltage conditions.

In yet another aspect, a thermistor 140 of FIG. 1 works with the fuel gauge 122 and provides over-temperature protection when the battery pack 110 is in a shut-down mode. The thermistor 140 may be PTC thermistor, which works in real time.

In further aspect, the fuel gauge 122 may include a temperature sensor, which senses the external temperature of the battery cells 112. Based on the external temperature, the fuel gauge 122 may perform corresponding safety functions as described herein.

Also, the fuel gauge 122 itself controls and senses the temperature of the charge/discharge FETs, has the ability to blow the a fuse (not shown), senses the current flowing the battery cells 112 by using a sense resistor (not shown), senses the temperature of the battery cell 112 with the thermistor 140, senses voltages of the battery cells 112 and the battery pack 110 with the pins in the array of contacts 144 (which are dedicated for informing the voltages of the battery cells 112 and the battery pack 110), detects and logs if the external over-voltage IC blows the fuse (not shown) externally, and detects when the battery cells 112 are grounded. By performing these safety functions, the fuel gauge 122 generally improves safety of the battery assembly 100.

In short, the battery cells 112 provide two levels of safety measures and there is another level of safety measure provided by the fuel gauge 122. These three levels of safety measures improve the safety of the battery assembly 100. However, the number of safety levels is not limited to three but can be expanded to more than three levels or reduced to less than three levels, as readily appreciated by a person of skill in the art.

The battery health module 330 may measure or check parameters related to the health of the battery cells 112. The parameters may relate to the remaining energy left in the battery cells 112, a count of recharges, a count of usage of the battery cells 112, internal voltage of the battery cells 112, temperature of the battery cells 112, etc. When the measured parameters are outside of the corresponding tolerance(s) or operational range(s), the fuel gauge 122 may interrupt operations to prevent irreparable damages to the battery assembly 100.

The adaptive battery input module 340 may be realized by a spanning input DC-DC converter topology. For example, the adaptive battery input module 340 may be a buck-boost converter, thereby allowing the input voltage to be greater than, equal to, or less than the desired output voltage. Here, the output voltage is independent from the input voltage. In other words, instead of the conventional power sources that are either voltage or current sources, the present disclosure provides an adaptive power source. In this way, the buck-boost converter may convert the input power source to a controlled and configurable output voltage source to deliver sufficient power needed for conditions and requirements of the battery assembly 100 and/or the connected device 250 (FIG. 2). The spanning input DC-DC converter may be a non-inverting buck-boost converter, single-ended primary-inductor converter (SEPIC), or Ćuk converter.

Figure 4B:
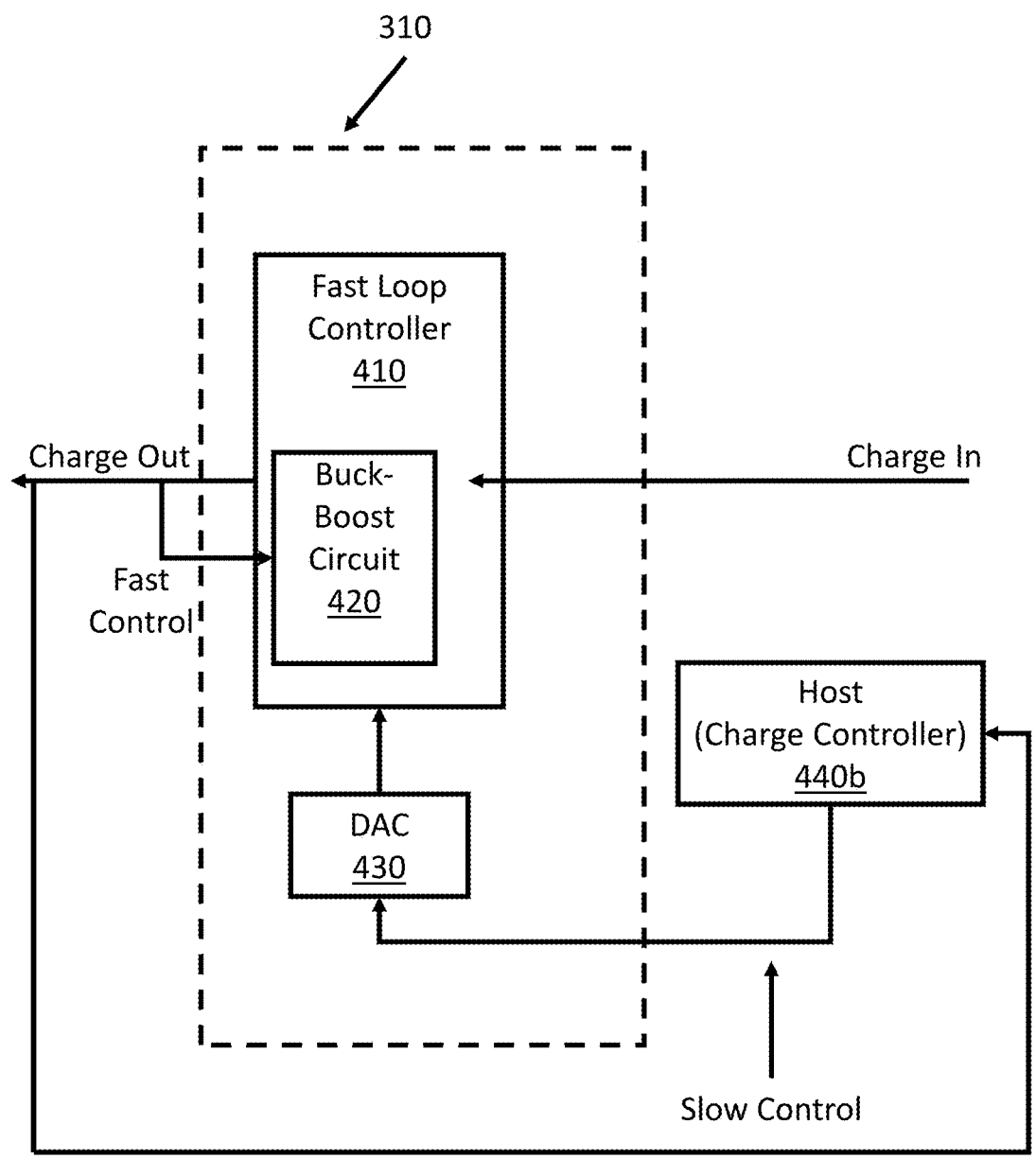

Turning to FIGS. 3 and 4B, the battery output control module 350 provides control functionalities for output voltage. The output voltage control may be performed in two ways (e.g., a slow mode and a fast mode). In the fast mode, the battery output control module 350 may internally control the converter 120 to compensate for load transients so that the converter 120 may provide the output voltage $V_{OUT}$ in a relatively short time. In this regard, the battery output control module 350 may include a fast loop controller 410, which includes a buck-boost circuit 420, for the fast control to compensate for the load transients.

In the slow mode, a host of the connected device 250 (FIG. 2) may measure the output voltage $V_{OUT}$, and provided the measured voltage to the battery output control module 350. By comparing the measured voltage with the required voltage from the connected device 250 (FIG. 2), the battery output control module 350 may control the converter 120 to amplify or decrease the output voltage $V_{OUT}$ by generating a feedback signal or PWM signal. There are analog-to-digital conversions in the host of the connected device 250 (FIG. 2) in measuring the output voltage $V_{OUT}$, and digital-to-analog conversions in the battery output control module 350 in converting the feedback signal or PWM signal into an analog signal to control the converter 120.

For the slow mode, the battery output control module 350 may include a digital-to-analog (DAC) converter 430. The battery output control module 350 controls the buck-boost circuit 420 to output voltage $V_{OUT}$. The host 440a (e.g., a generator) may monitor the output voltage $V_{OUT}$ and provide a feedback to the DAC 430 based on the level of the output voltage $V_{OUT}$. The DAC 430 converts the feedback signal, which is an analog signal, to a digital signal so as to control the operation of the buck-boost circuit 420.

In an aspect, the host of the connected device 250 (FIG. 2) may compare the measured voltage with the required voltage and provide the comparison result in a feedback signal to the battery output control module 350. In turn, the battery output control module 350 generates the PWM signal reflecting the feedback signal, and the converter 120 provides an updated voltage to the connected device 250 (FIG. 2). By controlling the output voltage $V_{OUT}$ in two different modes, the battery assembly 100 may promptly and reliably provide the required power to the connected device 250 (FIG. 2).

FIG. 5 illustrates a circuit diagram of a buck-boost converter of the battery assembly of FIG. 1, as an example of the spanning input DC-DC converter topology. The buck-boost converter 500 may have an h-bridge circuit, which has four switches 510-540. Each switch may be a FET or metal oxide semiconductor FET (MOSFET). When $V_{IN}$ is provided to the h-bridge, $V_{OUT}$ is outputted based on the control of the four switches 510-540.

The buck-boost converter 500 may also include an inductor 550, as a crossbar, connected to a connection between switches 510 and 520 and to a connection between the switches 530 and 540. When the required power by the connected device 250 (FIG. 2) is outside of the operational range of the battery pack 110, the inductor 550 may be scaled up or down to accommodate the power required by the connected device 250 (FIG. 2).

The buck-boost converter 500, when coupled with a low pass filter, presents variable impedance to a power source (e.g., the battery pack 110 of FIG. 1 or an external power source). The impedance is relative to the output power supplied by the buck-boost converter 500 as a function of the source characteristics. The circuit components shown in FIG. 5 are provided as an example. Various components can replace the circuit components of the buck-boost converter 500 and/or other structure may replace the buck-boost converter 500 to perform the same functions of the buck-boost converter 500 in accordance with this disclosure.

Figure 6A:
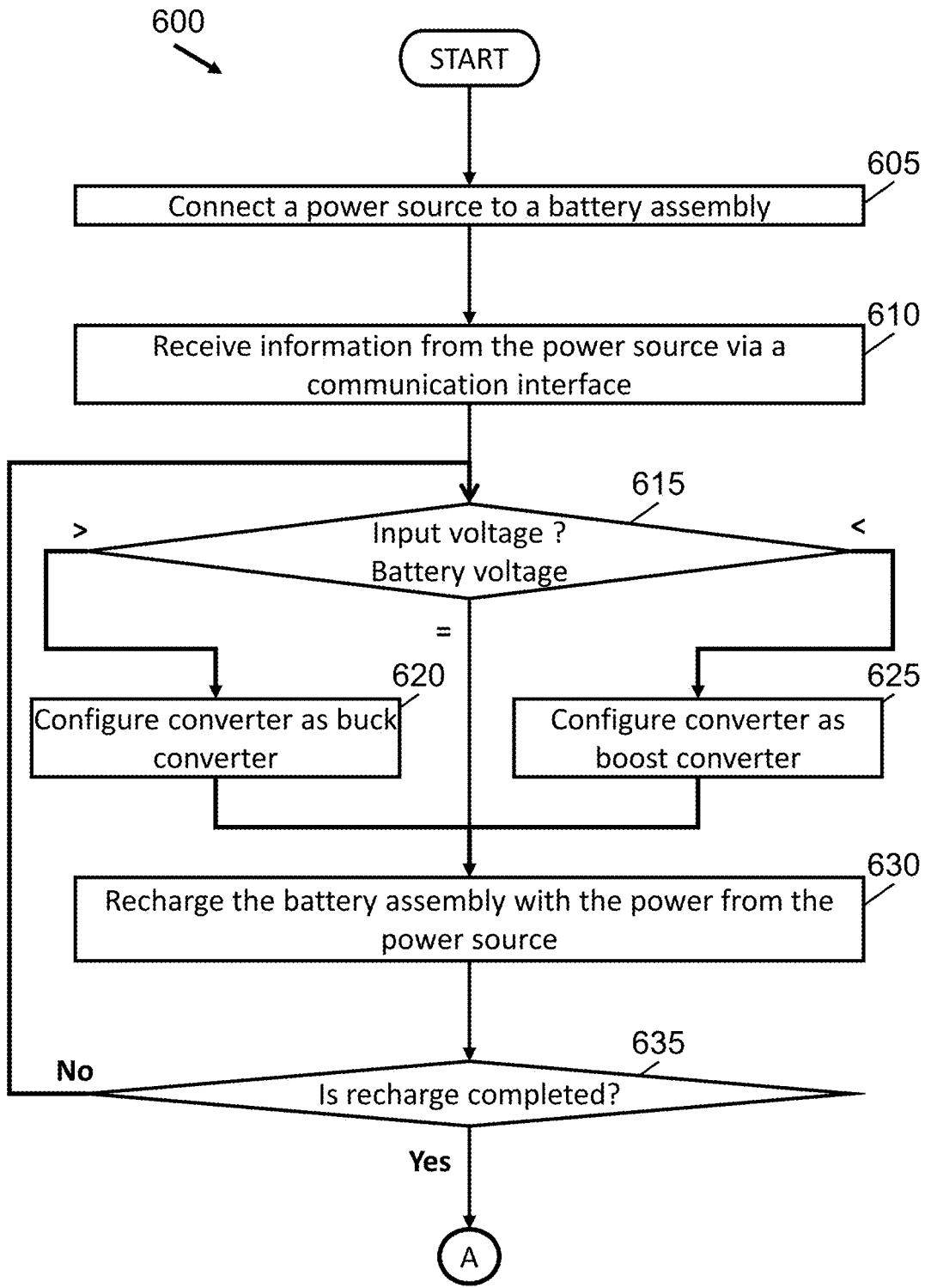
FIG. 6A is a flow diagram illustrating a method for recharging a battery assembly in accordance with the present disclosure.
Figure 6B:
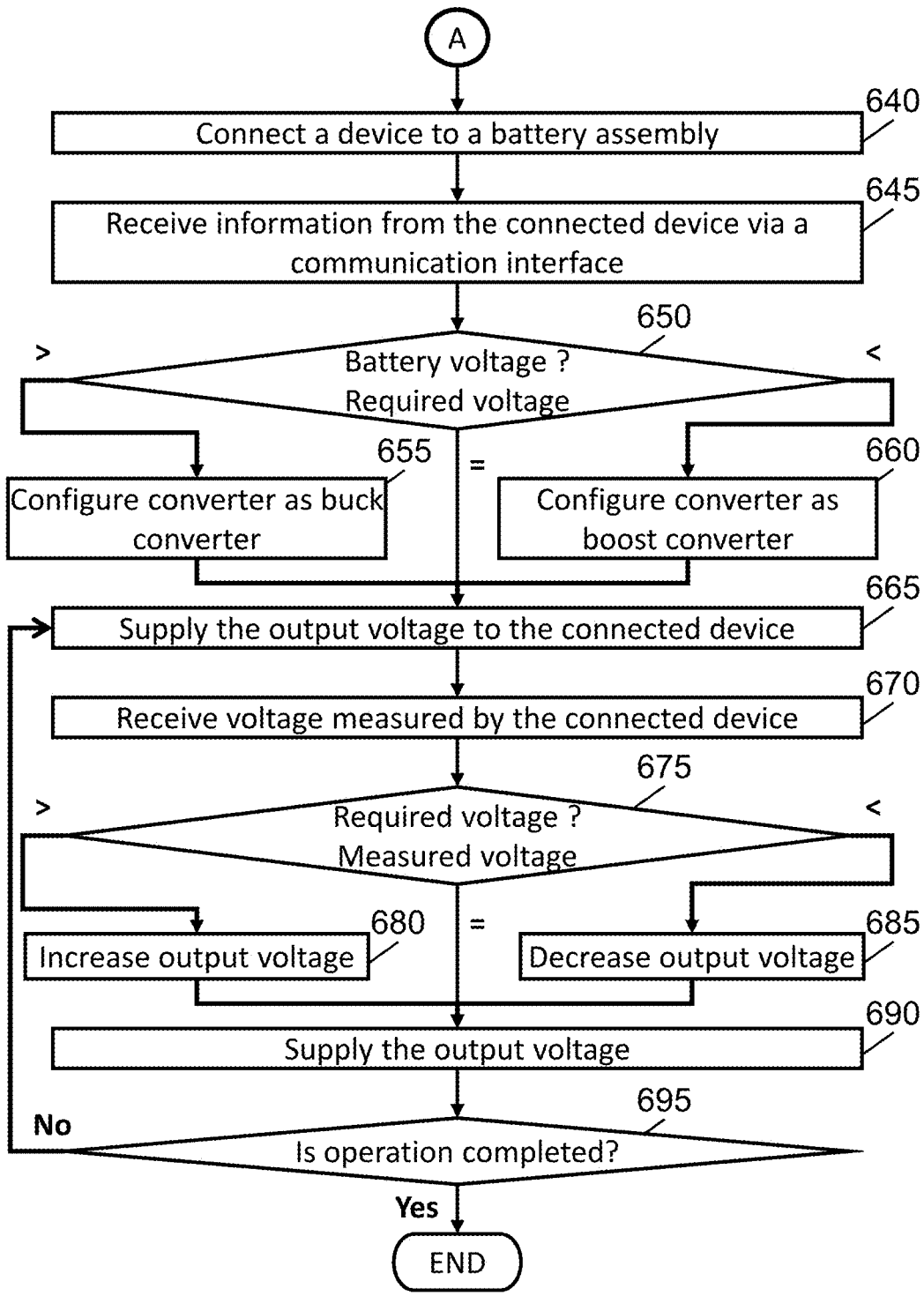
FIG. 6B is a flow diagram illustrating a method for controlling a battery assembly for a connected device in accordance with the present disclosure.

FIGS. 6A and 6B show a method 600 for controlling a battery assembly in accordance with embodiments of the present disclosure. In particular, FIG. 6A shows a recharge method for the battery assembly and FIG. 6B shows a supply method for controlling the battery assembly to supply power to a connected device. In an aspect, the recharge method and the supply method may be two parts of the method 600, as a whole. The recharge method may provide a substantially constant voltage to recharge the battery assembly, regardless of the different levels provided by different power sources. The control method may, likewise, supply a substantially constant output voltage to the connected device, regardless of different voltages required by different devices to be connected to the battery assembly.

The method 600 for recharging the battery assembly of the recharge method starts by connecting an external power source to the battery assembly in step 605. The external power source may provide a different level of power from another power source. The method 600 may accommodate the differences in the power level and provide a substantially constant voltage to the battery assembly. The constant voltage may be a desired voltage of the battery assembly.

In a case where the external power source is an AC source, the method 600 may include rectifying the AC to DC prior to step 605 or at any another suitable point.

In step 610, the battery assembly receives information from the external power source via a communication interface. The information may include an output voltage from the external power source, which is the input voltage to the battery assembly. In an aspect, the battery assembly may instantly measure the input voltage without receiving any information from the external power source (or in addition thereto) upon connection therebetween.

In step 615, the input voltage or the measured input voltage (both referred to herein as the "input voltage") is compared with the battery voltage, which is the constant voltage for recharging the battery assembly.

When the input voltage is determined to be greater than the battery voltage in step 615, the converter of the battery assembly is configured to be a buck converter in step 620. The buck converter decreases the input voltage to the battery voltage in step 620.

When the input voltage is determined to be less than the battery voltage in step 615, the converter of the battery assembly is configured to be a boost converter in step 620. The boost converter increases the input voltage to the battery voltage in step 625.

When the input voltage is determined to be equal to the battery voltage in step 615, the input voltage is not converted by the converter and is supplied to the battery assembly. After the converter is configured to be a buck converter or a boost converter in steps 620 and 625, respectively, the input voltage is converted to the battery voltage. Then, in step 630, the battery voltage recharges the battery assembly, specifically, one or more battery cells in the battery assembly.

In step 635, it is determined whether the recharge is completed. When it is determined that the recharge is incomplete, the recharge method keeps recharging the battery assembly until the battery assembly is fully charged.

In an aspect, when it is determined that the recharge is incomplete, the recharge method may repeatedly go back to step 615 to keep tracking the level of input voltage with respect to the battery voltage until the battery assembly is fully charged.

When it is determined that the battery assembly is fully charged, the recharge method is ended. Or, the method 600 may proceed to the supply method as illustrated in FIG. 6B.

The supply method starts with connecting a device to a battery assembly in step 640. Through a communication interface between the battery assembly and the connected device, the battery assembly receives information from the connected device in step 645. The received information may provide specifications required by the connected device. For example, required voltage, required current, required power, or any combination thereof may be included in the information. Further, the information may include a type of the connected device (e.g., surgical device or non-surgical device, the type of surgical or non-surgical device, etc.), model name of the connected device, etc.

In step 650, the battery voltage is compared with the required voltage obtained from the received information. In an aspect, if the connected device requires a current rather than a voltage, the battery current may be compared with the required current in step 650. Likewise, power may be compared in step 650. Or any other values may be compared in step 650 to adequately supply energy to the connected device without departing the spirit of this disclosure.

When the battery voltage is determined to be greater than the required voltage in step 650, the converter may be configured to be a buck converter in step 655. Or when the battery voltage is determined to be less than the required voltage in step 650, the converter may be configured to be a boost converter in step 660.

When the battery voltage is determined to be equal to the required voltage in step 650, the converter does not increase or decrease the battery voltage.

The converter, as configured or not, then outputs and supplies the converted voltage to the connected device in step 665. Even if the converter is configured to output the required voltage, the actual voltage supplied by the converter might not be equal to the required voltage due to, e.g., parasitic drain inside or outside of the battery assembly and the connected device.

In an aspect, the battery assembly may internally check whether the output voltage is less than the required voltage. If less, then the battery assembly may perform steps 650-660 in a fast mode so that the converter outputs a voltage close to the required voltage in a short time.

The connected device may measure the output voltage from the battery assembly and provide the measured voltage to the battery assembly, and the battery assembly may in turn receive the measured voltage from the connected device in step 670. Alternatively, the battery assembly may measure the output voltage supplied to the connected device.

Thus, in step 670, the measured voltage can be obtained by the battery assembly and not from the connected device. This may be used for devices which are unable to communicate with the battery assembly.

In step 675, the required voltage is compared with the measured voltage. When it is determined that the required voltage is greater than the measured voltage, the battery assembly may increase the output voltage in step 680. This can be done by increasing the duty cycle of an h-bridge of the converter. PWM signals may be used to control the duty cycle.

In another embodiment, the connected device may compare the required voltage with the measured voltage and provide a feedback signal informing the battery assembly of the comparison. The battery assembly may then generate the PWM signal or any control signal to accommodate the difference between the required voltage and the measured voltage.

When it is determined that the required voltage is less than the measured voltage, the battery assembly may decrease the output voltage in step 680. This can be done by decreasing the duty cycle of the h-bridge of the converter.

When the required voltage is determined to be equal to the measured voltage, the converter does not increase or decrease the output voltage. In step 690, the output voltage is supplied to the connected device so that the connected device performs its intended operations.

In step 695, it is determined whether or not the operation is done by the connected device. When the operation is not completed, the supply method keeps performing steps 665-695 until the operation is completed. When the operation is determined to be completed, the supply method is ended. Steps 665-695 are done in a slower pace than the fast mode.

Figure 7:
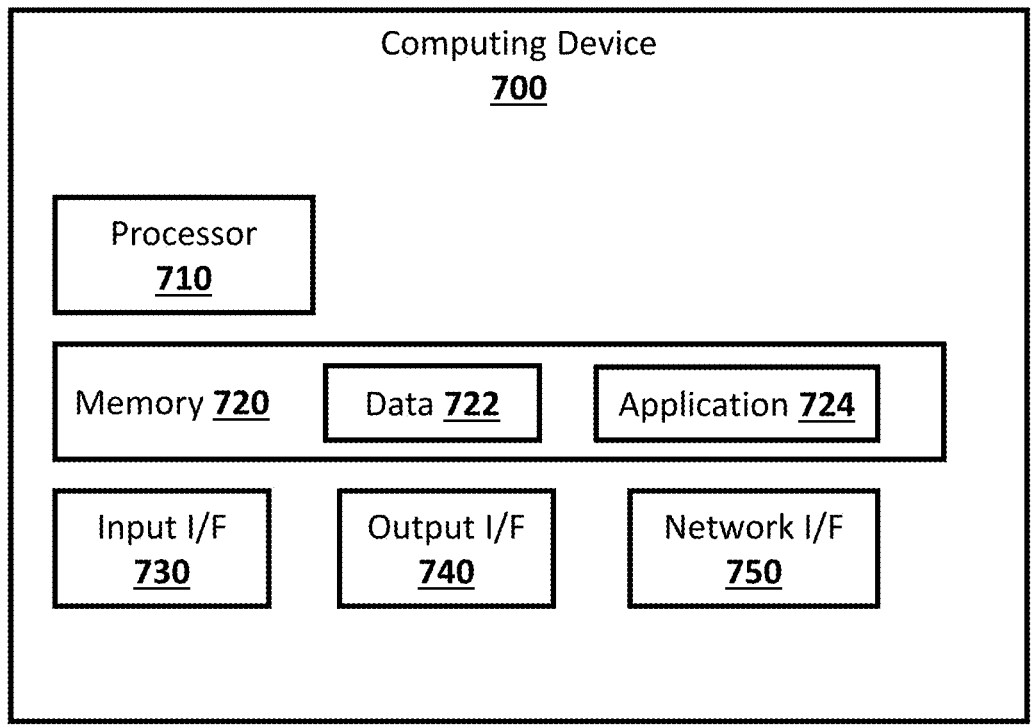
FIG. 7 is a block diagram illustrating a computing device in accordance with the present disclosure.

Referring now to FIG. 7, a schematic diagram of a computing device is shown and designated generally as a computing device 700. Though not explicitly shown in the corresponding figures of the present application, the computing device 700, or one or more components thereof, may represent one or more components (e.g., the processor of the fuel gauge 122) of the battery assembly 100 of FIG. 1. The computing device 700 may include one or more processors 710, memories 720, input interfaces 730, output interfaces 740, network interfaces 750, or any desired subset of components thereof.

The memory 720 includes non-transitory computer-readable storage media for storing data and/or software which include instructions that may be executed by the one or more processors 710. When executed, the instructions may cause the processor 710 to control operation of the computing device 700 such as, without limitation, reception, analysis, and transmission of sensor signals received in response to voltage, current, and power received from an external power source or supplied by the battery assembly 100. In embodiments, the memory 720 includes non-transitory computer-readable storage media for storing data and/or software which includes instructions that may be executed by the one or more processors 710. The memory 720 may store programmable configuration file for the battery assembly. For example, the programmable configuration file may include characteristics of the battery assembly 100 (e.g., the size of each battery cell 112, capacity of the battery pack 110, the number of battery cells 112 in the battery pack 110, the model name of the battery pack 110 or the battery cells 112, types of battery cells 112, safety feature variants, predetermined designations of parameters, etc. The type of battery cells 112 may identify the chemistry such as, for example, lithium-ion, lead acid gel, nickel-cadmium, nickel metal hybrid, or any other type of battery, which can be readily appreciated by a person of ordinary skill in the art.

The programmable configuration file may be revised, updated, or changed automatically or by a user in a case when the characteristics of the battery assembly 100 are changed. For example, if the number of battery cells is changed, then the corresponding value in the programmable configuration file is changed. Further, when the internal voltage of the battery assembly 100 is changed due to the change in the number of battery cells 112, the corresponding value in the programmable configuration file is likewise changed or updated.

Further, in a case when a resistor value is changed to adapt to various external power source, the corresponding value may be updated, correspondingly.

Furthermore, the number of usages of the battery assembly 100 may be updated after each usage in the programmable configuration file.

The memory 720 may include one or more solid-state storage devices such as flash memory chips. Additionally, or alternatively, the memory 720 may include one or more mass storage devices in communication with the processor 710 through a mass storage controller and a communications bus (not shown). Although the description of computer readable media described in this disclosure refers to a solid-state storage device, it will be appreciated by one of ordinary skill that computer-readable media may include any available media that can be accessed by the processor 710. More particularly, the computer readable storage media may include, without limitation, non-transitory, volatile, non-volatile, removable, non-removable media, and the like, implemented in any method of technology for storage of information such as computer readable instructions, data structures, program modules, or other suitable data access and management systems. Examples of computer-readable storage media include random access memory (RAM), read-only member (ROM), erasable programmable read-only memory (EPROM), electronically erasable programmable read-only memory (EEPROM), flash memory, or other known solid state memory technology, compact disk ROM (CD-ROM), digital versatile disk (DVD), Blu-Ray, or other such optical storage, magnetic cassettes, magnetic tape, magnetic disk storage or other magnetic storage devices, or any other medium which may be used to store information and which can be accessed by the computing device 700.

In embodiments, the memory 720 stores data 722 and/or one or more applications 724. Such applications 724 may include instructions which are executed by the one or more processors 710 of the computing device 700. The applications 724 may include instructions which cause an input interface 730 and/or an output interface 740 to receive and transmit sensor signals, respectively, to and from the various components of the battery assembly 100. Additionally or alternatively, the computing device 700 may transmit the signals for analysis and/or display via the output interface 740.

The memory 720 may further transmit and/or receive data via a network interface 750 via one or more wireless configurations, e.g., radio frequency, optical, Wi-Fi®, Bluetooth® (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE® 802.15.4-2003 standard for wireless personal area networks (WPANs)). Although depicted as a separate component, the network interface 750 may be integrated into the input interface 730 and/or the output interface 740.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A battery assembly, comprising:
a battery pack configured to supply energy to a load having a required energy;
a housing enclosing the battery pack therein;
a converter configured to convert an internal energy of the battery pack; and
a controller configured to adjust a parameter of the converter based on information received from the load via a communication interface such that the converter converts the internal energy to the energy required by the load,
wherein the converted internal energy is supplied to the load as the supplied energy,
wherein the controller measures parameters of the supplied energy, compares the measured parameters with reference values included in the information, and controls the converter to adjust a level of the supplied energy,
wherein the converter includes an H-bridge with an inductor as a crossbar, and
wherein the inductor is to be scaled to accommodate energy required by the load when the required energy is outside of an operational range of the battery pack.

2. The battery assembly according to claim 1, wherein the converter is a buck-boost converter.

3. The battery assembly according to claim 2, wherein the controller controls the H-bridge to configure the converter into a buck converter or a boost converter based on comparison between the internal energy and the required energy.

4. The battery assembly according to claim 1, wherein the load is a surgical device.

5. The battery assembly according to claim 1, further comprising a memory configured to store a programmable configuration file, which includes a plurality of settings of the converter.

6. The battery assembly according to claim 5, wherein the plurality of settings included in the programmable configuration file are modified according to characteristics of the battery assembly.

7. The battery assembly according to claim 6, wherein the characteristics include a size of a battery cell in the battery pack, a chemistry of the battery cell in the battery pack, and tolerance ranges of the battery pack.

8. The battery assembly according to claim 1, further comprising a sensor configured to sense the supplied energy to the load to generate sensed results.

9. The battery assembly according to claim 8, wherein the controller is further configured to measure at least one of a voltage or a current the supplied energy based on the sensed results.

10. The battery assembly according to claim 9, wherein the controller is further configured to compare the measurement with the required energy and generate a feedback signal to control the converter based on the feedback signal.

11. The battery assembly according to claim 1, wherein the controller generates a pulse-width-modulation (PWM) signal to adjust a duty cycle of the H-bridge.

12. The battery assembly according to claim 1, further comprising a safety device configured to stop delivery of the supplied energy to the load in an emergency condition.

13. The battery assembly according to claim 12, wherein the emergency condition occurs when a current of the supplied energy falls outside of an operable current range or when a temperature of the battery pack falls outside of an operable temperature range.

14. The battery assembly according to claim 12, wherein the safety device is a separator between an anode and a cathode of the battery pack.

15. The battery assembly according to claim 12, wherein the safety device is a pressure relief vent configured to open a connection between internal and external positive terminals of the battery pack when a heat generated by the battery pack causes a pressure within the battery pack to go over a threshold pressure.

16. A method for controlling a battery assembly including a battery pack and a converter, the method comprising:
connecting the battery assembly to a load, the load having a required energy;
receiving information from the load via a communication interface between the battery assembly and the load;
comparing an internal energy of the battery assembly with the required energy of the load, which is obtained from the information;
configuring the converter of the battery assembly as a buck converter or a boost converter based on the comparison; and
controlling the converter to supply energy, as a supplied energy, to the load via an output port,
wherein controlling the converter includes:
measuring parameters of the supplied energy;
comparing the measured parameters with reference values included in the information; and
controlling the converter to adjust a level of the supplied energy,
wherein the converter includes an H-bridge with an inductor as a crossbar, and
wherein the method further comprises:
scaling the inductor to accommodate energy required by the load when the required energy is outside of an operational range of the battery pack.

17. The method according to claim 16, further comprising:
sensing parameters of the supplied energy to generate a feedback signal; and
controlling the converter based on the feedback signal so that a voltage of the supplied energy follows a voltage of the required energy.

18. The method according to claim 17, further comprising generating a pulse-width-modulation (PWM) signal based on the feedback signal,
wherein a duty cycle of the H-bridge is adjusted based on the PWM signal.

19. The method according to claim 16, further comprising:
stopping supply of the supplied energy when an emergency occurs.

20. The method according to claim 19, wherein the emergency occurs when a current of the supplied energy goes over a threshold current or when a temperature of the battery assembly is over a threshold temperature.

21. A portable surgical system comprising:
a surgical device requiring a required energy to perform a surgical operation; and
a battery assembly configured to couple to the surgical device and provide the required energy to the surgical device, the battery assembly comprising:
a battery pack configured to supply energy to the surgical device;
a housing enclosing the battery pack therein;
a converter configured to convert an internal energy of the battery pack; and
a controller configured to adjust a parameter of the converter based on information received from the surgical device via a communication interface such that the converter converts the internal energy to the energy required by the surgical device,
wherein the converted internal energy is supplied to the surgical device as the supplied energy,
wherein the controller measures parameters of the supplied energy, compares the measured parameters with reference values included in the information, and controls the converter to adjust a level of the supplied energy,
wherein the converter includes an H-bridge with an inductor as a crossbar, and
wherein the inductor is to be scaled to accommodate energy required by the surgical device when the required energy is outside of an operational range of the battery pack.

* * * * *